United States Patent
Oft et al.

(10) Patent No.: US 9,364,517 B2
(45) Date of Patent: Jun. 14, 2016

(54) METHOD OF TREATMENT OF LYMPHOMA WITH PEGYLATED IL-10

(71) Applicant: Merck Sharp & Dohme Corp., Rahway, NJ (US)

(72) Inventors: Martin Oft, Palo Alto, CA (US); Catherine Sheppard, San Francisco, CA (US); John Brian Mumm, Los Altos Hills, CA (US); Lingling Wu, Palo Alto, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/485,315

(22) Filed: Sep. 12, 2014

(65) Prior Publication Data

US 2015/0079031 A1    Mar. 19, 2015

Related U.S. Application Data

(63) Continuation of application No. 12/976,063, filed on Dec. 22, 2010, now Pat. No. 8,865,652, which is a continuation of application No. 12/463,825, filed on May 11, 2009, now abandoned, which is a continuation of application No. 11/862,626, filed on Sep. 27, 2007, now abandoned.

(60) Provisional application No. 60/915,603, filed on May 2, 2007, provisional application No. 60/848,326, filed on Sep. 28, 2006.

(51) Int. Cl.
| | |
|---|---|
| *A61P 35/00* | (2006.01) |
| *A61K 45/00* | (2006.01) |
| *A61K 47/48* | (2006.01) |
| *A61K 38/20* | (2006.01) |
| *C12P 21/00* | (2006.01) |
| *A61K 45/06* | (2006.01) |

(52) U.S. Cl.
CPC ............. *A61K 38/2066* (2013.01); *A61K 45/06* (2013.01); *A61K 47/48215* (2013.01)

(58) Field of Classification Search
None
See application file for complete search history.

(56) References Cited

U.S. PATENT DOCUMENTS

| | | | |
|---|---|---|---|
| 5,624,823 A | 4/1997 | Sachs et al. | |
| 5,665,345 A | 9/1997 | Yarchoan et al. | |
| 5,824,784 A | 10/1998 | Kinstler et al. | |
| 5,866,134 A | 2/1999 | Fine et al. | |
| 5,989,867 A | 11/1999 | Knappe et al. | |
| 6,217,857 B1 | 4/2001 | Mosmann et al. | |
| 6,387,364 B1 | 5/2002 | Ferguson | |
| 6,660,258 B1 | 12/2003 | Tovey | |
| 6,770,272 B2 | 8/2004 | Strom et al. | |
| 6,989,377 B2 | 1/2006 | Hayes et al. | |
| 7,052,686 B2 | 5/2006 | Lee et al. | |
| 7,261,882 B2 | 8/2007 | Watkins | |
| 7,749,490 B2 | 7/2010 | Sommer et al. | |
| 7,939,056 B2 | 5/2011 | Horwitz et al. | |
| 2002/0044921 A1 | 4/2002 | Lee et al. | |
| 2003/0186386 A1 | 10/2003 | Hansen et al. | |
| 2005/0260767 A1 | 11/2005 | Clerici et al. | |
| 2006/0046961 A1 | 3/2006 | McKay et al. | |
| 2008/0058246 A1 | 3/2008 | Bhaskaran et al. | |
| 2008/0069797 A1 | 3/2008 | Roncarolo et al. | |
| 2010/0068147 A1 | 3/2010 | Hibberd et al. | |
| 2010/0111898 A1 | 5/2010 | Pelura | |
| 2010/0297070 A1 | 11/2010 | Dugan et al. | |

FOREIGN PATENT DOCUMENTS

| | | |
|---|---|---|
| WO | WO 9212725 | 8/1992 |
| WO | WO 9212726 | 8/1992 |
| WO | WO 9519780 | 7/1995 |
| WO | WO 9703690 | 2/1997 |
| WO | WO 01005821 | 1/2001 |
| WO | WO 2004044006 | 5/2004 |
| WO | WO 2006119170 | 11/2006 |

OTHER PUBLICATIONS

Berman et al. (1996) "Systemic administration of cellular IL-10 induces an effective, specific, and long-lived immune response against established tumors in mice" *J Immunol* 157:231-238.
Cannistra & Niloff (1996) "Cancer of the uterine cervix." *New Engl J Med* 334:1030-1038.
Chen & Zlotnik (1991) "IL-10: a novel cytotoxic T cell differentiation factor" *J Immunol* 147:528-534.
Davidson & Diamond (2001) "Autoimmune diseases" *New Engl J Med* 345:340-350.
Enzinger & Mayer (2003) "Esophageal cancer" *New Engl J Med* 349:2241-2252.
Farrar et al. (1999) "Cancer dormancy. VII. A regulatory role for CD8+ T cells and IFN-gamma in establishing and maintaining the tumor-dormant state" *J Imunol* 162:2842-2849.
Fiorentino et al. (1989) "Two types of mouse T helper cell. IV. Th2 clones secrete a factor that inhibits cytokine production by Th1 clones" *J Exp Med* 170:2081-2095.
Forastiere et al. (2001) "Head and neck cancer" *New Engl J Med* 345:1890-1900.
GenBank Accession No. M37897 "Mouse interleukin 10 mRNA, complete cds" dated Apr. 27, 1993.
GenBank Accession No. NP_000563 "interleukin-10 precursor [*Homo sapiens*]" dated Mar. 3, 1995.
Groux et al. (1998) "A transgenic model to analyze the immunoregulatory role of IL-10 secreted by antigen-presenting cells" *J Immunol* 162:1723-1729.
Groux et al. (1998) "Inhibitory and stimulatory effects of IL-10 on human CD8+ T cells" *J Immunol* 160:3188-3193.

(Continued)

*Primary Examiner* — Elly-Gerald Stoica
(74) *Attorney, Agent, or Firm* — Carol L. Francis; Bozicevic, Field & Francis LLP

(57) ABSTRACT

Provided are methods of treatment for tumors. In particular, methods are provided for use of a chemically modified IL-10 to treat tumors.

16 Claims, No Drawings

(56) References Cited

OTHER PUBLICATIONS

Hagenbaugh et al. (1997) "Altered immune responses in interleukin 10 transgenic mice" *J Exp Med* 185:2101-2110.

Huang et al. (1996) "Interleukin 10 Suppresses Tumor Growth and Metastasis of Human Melanoma Cells: Potential Inhibition of Angiogenesis" Clinical Cancer Research, The American Assn for Cancer Research 2(12):1969-1979.

Ishikawa et al. (2005) "Interleukin-10 plasmid DNA inhibits liver and lung metastasis of Colon 26 adenocarcinoma in mice" Proceedings of the Annual Meeting, American Association for Cancer Research 46:792-793.

Izbicki et al. (1997) "Prognostic value of immunohistochemically identifiable tumor cells in lymph nodes of patients with completely resected esophageal cancer" *New Engl J Med* 337:1188-1194.

Katre (1993) "The Conjugation of Proteins with Polyethylene Glycol and Other Polymers Altering Properties of Proteins to Enhance their Therapeutic Potential" *Advanced Drug Delivery Reviews* 10(1):91-114.

Kokura et al. (2003) "The blocking of NFkB activation by systemic interleukin-10 gene therapy inhibits liver and lung metastasis of colon 26 adenocarcinoma in mice" Gastroenterology 124(4):A603.

Kundu et al. (1996) "Antimetastatic and antitumor activities of interleukin 10 in a murine model of breast cancer" *J Natl Cancer Inst* 88:536-541.

Kundu et al. (1997) "Interleukin-10 inhibits tumor metastasis, down regulates MHC class I, enhances NK lysis" Cellular Immunology, Academic Press 180(1):55-61.

Le et al. (2001) "Pre-existing tumor-sensitized T cells are essential for eradication of established tumors by IL-12 and cyclophosphamide plus IL-12" *J Immunol* 167:6765-6772.

Lu et al. (2004) "Prognostic factors in resected stage I non-small-cell lung cancer: a multivariate analysis of six molecular markers" *J Clin Oncol* 22:4575-4583.

Lynch & Chapelle (2003) "Hereditary colorectal cancer" *New Engl J Med* 348:919-932.

Miki et al. (2000) "Anti-metastatic effect of IL-10 gene modification in human lung cancer cells is differentially regulated by organ microenvironments" Proceedings of the Annual Meeting, American Association for Cancer Research 41:3.

Osborne (1998) "Tamoxifen in the treatment of breast cancer" *New Engl J Med* 339:1609-1618.

Ramirez-Montagut et al. (2003) "Immunity to melanoma: unraveling the relation of tumor immunity and autoimmunity" *Oncogene* 22:3180-3187.

Sakamoto et al. (2003) "Interleukin-10 gene therapy enhances antitumor effect of CPT-11 for lung metastasis of colon 26 adenocarcinoma in mice" Gastroenterology 124(4):A456.

Sawaya et al. (2003) "Risk of cervical cancer associated with extending the interval between cervical-cancer screenings" *New Engl J Med* 349:1501-1509.

Smith et al. (1996) "Administration of interleukin-10 at the time of priming protects Corynebacterium parvum-primed mice against LPS- and TNF-alpha-induced lethality" *Cellular Immunology* 173(2):207-214.

Syto et al. (1998) "Structural and biological stability of the human interleukin 10 homodimer" *Biochemistry* 37(48):16943-16951.

Von Andrian & Mackay (2000) "T-cell function and migration. Two sides of the same coin" New Engl J Med 343:1020-1034.

Zheng et al. (1996) "Interleukin-10 inhibits tumor metastasis through an NK cell-dependent mechanism" *J Exp Med* 184:579-584.

METHOD OF TREATMENT OF LYMPHOMA WITH PEGYLATED IL-10

This application is a Continuation of U.S. patent application Ser. No. 12/976,063, filed Dec. 22, 2010, now issued as U.S. Pat. No. 8,865,652, which is a Continuation of U.S. patent application Ser. No. 12/463,825 filed May 11, 2009, now abandoned, which is a Continuation of U.S. patent application Ser. No. 11/862,626 filed Sep. 27, 2007, now abandoned, which claims benefit of U.S. Provisional patent application No. 60/915,603, filed May 2, 2007 and claims benefit of U.S. Provisional patent application No. 60/848,326, filed Sep. 28, 2006, all of which are hereby incorporated by reference in their entirety.

FIELD OF THE INVENTION

The present invention concerns uses of mammalian cytokine molecules and related reagents. More specifically, the invention relates to identification of chemically modified mammalian cytokine proteins that can be used in the treatment of proliferative disorders.

BACKGROUND OF THE INVENTION

Cancers and tumors can be controlled or eradicated by the immune system. The immune system includes several types of lymphoid and myeloid cells, e.g., monocytes, macrophages, dendritic cells (DCs), eosinophils, T cells, B cells, and neutrophils. These lymphoid and myeloid cells produce secreted signaling proteins known as cytokines. The cytokines include, e.g., interleukin-10 (IL-10), interferon-gamma (IFNγ), IL-12, and IL-23. Immune response includes inflammation, i.e., the accumulation of immune cells systemically or in a particular location of the body. In response to an infective agent or foreign substance, immune cells secrete cytokines which, in turn, modulate immune cell proliferation, development, differentiation, or migration. Excessive immune response can produce pathological consequences, such as autoimmune disorders, whereas impaired immune response may result in cancer. Anti-tumor response by the immune system includes innate immunity, e.g., as mediated by macrophages, NK cells, and neutrophils, and adaptive immunity, e.g., as mediated by antigen presenting cells (APCs), T cells, and B cells (see, e.g., Abbas, et al. (eds.) (2000) *Cellular and Molecular Immunology*, W.B. Saunders Co., Philadelphia, Pa.; Oppenheim and Feldmann (eds.) (2001) *Cytokine Reference*, Academic Press, San Diego, Calif.; von Andrian and Mackay (2000) *New Engl. J. Med.* 343:1020-1034; Davidson and Diamond (2001) *New Engl. J. Med.* 345:340-350).

Methods of modulating immune response have been used in the treatment of cancers, e.g., melanoma. These methods include treatment either with cytokines such as IL-2, IL-10, IL-12, tumor necrosis factor-alpha (TNFalpha), IFNγ, granulocyte macrophage-colony stimulating factor (GM-CSF), and transforming growth factor (TGF), or with cytokine antagonists (e.g., antibodies). Interleukin-10 was first characterized as a cytokine synthesis inhibitory factor (CSIF; see, e.g., Fiorentino, et al (1989) *J. Exp. Med.* 170:2081-2095). IL-10 is a pleiotropic cytokine produced by T cells, B cells, monocytes, that can function as both an immunosuppressant and immunostimulant (see, e.g., Groux, et al. (1998) *J. Immunol.* 160:3188-3193; and Hagenbaugh, et al. (1997) *J. Exp. Med.* 185:2101-2110).

Animal models suggest that IL-10 can induce NK-cell activation and facilitate target-cell destruction in a dose-dependent manner (see, e.g., Zheng, et al. (1996) *J. Exp. Med.* 184:579-584; Kundu, et al. (1996) *J. Natl. Cancer Inst.* 88:536-541). Further studies indicate that the presence of IL-10 in the tumor microenvironment correlates with better patient survival (see, e.g., Lu, et al. (2004) *J. Clin. Oncol.* 22:4575-4583).

Unfortunately, the serum half life for IL-10 is relatively short, i.e., 2-6 hours (see, e.g., Smith et al. (1996) *Cellular Immunol.* 173:207-214). The present invention addresses this problem by providing methods of using an engineered form of IL-10, e.g., a pegylated IL-10, to treat cancer. In addition to a longer serum half life, the pegylated form of IL-10 surprisingly exhibited increased tumor killing activity, for example, through increased recruitment of CD8+ T cells to the tumor site, when compared to non-pegylated IL-10.

SUMMARY OF THE INVENTION

The present invention is based upon the discovery that pegylated IL-10 is an improved modulator of tumor growth. The present invention provides method of inhibiting or reducing growth of a tumor or cancer comprising contacting the tumor with an effective amount of a pegylated interleukin-10 (PEG-IL-10). In one embodiment, the PEG-IL-10 is mono-PEG-IL-10. The PEG-IL-10 comprises an SC-PEG-12K linker. In an alternative embodiments the PEG-IL-10 comprises a methoxy-PEG-aldehyde (PALD-PEG) linker. In certain embodiments the PALD-PEG linker comprises a PEG molecule having a molecular weight selected from the group consisting 5 KDa, 12 KDa, or 20 KDa. The PEG-IL-10 inhibits growth of the tumor or cancer or the PEG-IL-10 reduces the size of the tumor or cancer. The PEG-IL-10 increases infiltration of CD8+ T cells into the tumor when compared to non-pegylated IL-10. In another embodiment, PEG-IL-10 increases the expression of at least one inflammatory cytokine, which can be selected from the group consisting of IFNγ, IL-4, IL-6, IL-10, and RANK-ligand (RANK-L). In certain embodiments, the PEG-IL-10 is co-administered with at least one chemotherapeutic agent. The chemotherapeutic agent can be at least one of the chemotherapeutic agents of Table 16. In certain embodiments, the tumor or cancer is selected from the group consisting of colon cancer, ovarian cancer, breast cancer, melanoma, lung cancer, glioblastoma, and leukemia.

The present invention encompasses a method of treating a subject suffering from a cancer or tumor comprising administering to the subject an effective amount of PEG-IL-10. In one embodiment, the PEG-IL-10 is mono-PEG-IL-10. The PEG-IL-10 comprises an SC-PEG-12K linker. In another embodiment, the PEG-IL-10 comprises a methoxy-PEG-aldehyde (PALD-PEG) linker which can have a molecular weight selected from the group consisting 5 KDa, 12 KDa, or 20 KDa. PEG-IL-10 inhibits growth of the cancer or tumor or reduces the size of the tumor or cancer. PEG-IL-10 increases infiltration of CD8+ T cells into the tumor when compared to non-pegylated IL-10. In another embodiment, PEG-IL-10 increases the expression of at least one inflammatory cytokine. The inflammatory cytokine is selected from the group consisting of IFNγ, IL-4, IL-6, IL-10, and RANK-L. In certain embodiments, the PEG-IL-10 is co-administered with at least one chemotherapeutic agent. The chemotherapeutic agent can be at least one of the chemotherapeutic agents of Table 16. PEG-IL-10 reduces metastasis of a cancer or tumor. In a further embodiment, the tumor or cancer is selected from the group consisting of colon cancer, ovarian cancer, breast cancer, lung cancer, melanoma, glioblastoma, and leukemia. In certain embodiments, the subject being treated is human. and the PEG-IL-10 is human PEG-hIL-10 (PEG-hIL-10).

DETAILED DESCRIPTION

As used herein, including the appended claims, the singular forms of words such as "a," "an," and "the," include their corresponding plural references unless the context clearly dictates otherwise. All references cited herein are incorporated by reference to the same extent as if each individual publication, patent application, or patent, was specifically and individually indicated to be incorporated by reference.

I. Definitions

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compositions derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Proliferative activity" encompasses an activity that promotes, that is necessary for, or that is specifically associated with, e.g., normal cell division, as well as cancer, tumors, dysplasia, cell transformation, metastasis, and angiogenesis.

"Administration" and "treatment," as it applies to an animal, human, experimental subject, cell, tissue, organ, or biological fluid, refers to contact of an exogenous pharmaceutical, therapeutic, diagnostic agent, compound, or composition to the animal, human, subject, cell, tissue, organ, or biological fluid. "Administration" and "treatment" can refer, e.g., to therapeutic, placebo, pharmacokinetic, diagnostic, research, and experimental methods. "Treatment of a cell" encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of PEG-IL-10 to a human or animal subject, a cell, tissue, physiological compartment, or physiological fluid. "Treatment of a cell" also encompasses situations where PEG-IL-10 contacts IL-10 receptor (heterodimer of IL-10R1 and IL-10R2) e.g., in the fluid phase or colloidal phase, as well as situations where an IL-10 agonist or antagonist contacts a fluid, e.g., where the fluid is in contact with a cell or receptor, but where it has not been demonstrated that the agonist or antagonist directly contacts the cell or receptor.

"Cachexia" is a wasting syndrome involving loss of muscle (muscle wasting) and fat, resulting from a disorder in metabolism. Cachexia occurs in various cancers ("cancer cachexia"), chronic pulmonary obstructive disorder (COPD), advanced organ failure, and AIDS. Cancer cachexia is characterized by, e.g., marked weight loss, anorexia, asthenia, and anemia. Anorexia is a disorder resulting from lack of motivation to eat, e.g., food aversion (see, e.g., MacDonald, et al. (2003) *J. Am. Coll. Surg.* 197:143-161; Rubin (2003) *Proc. Natl. Acad. Sci. USA* 100:5384-5389; Tisdale (2002) *Nature Reviews Cancer* 2:862-871; Argiles, et al. (2003) *Drug Discovery Today* 8:838-844; Lelli, et al. (2003) *J. Chemother.* 15:220-225; Argiles, et al. (2003) *Curr. Opin. Clin. Nutr. Metab. Care* 6:401-406).

"Conservatively modified variants of PEG-IL-10" applies to both amino acid and nucleic acid sequences. With respect to particular nucleic acid sequences, conservatively modified variants refers to those nucleic acids which encode identical or essentially identical amino acid sequences or, where the nucleic acid does not encode an amino acid sequence, to essentially identical nucleic acid sequences. Because of the degeneracy of the genetic code, a large number of functionally identical nucleic acids may encode any given protein.

As to amino acid sequences, one of skill will recognize that an individual substitution to a nucleic acid, peptide, polypeptide, or protein sequence which substitutes an amino acid or a small percentage of amino acids in the encoded sequence for a conserved amino acid is a "conservatively modified variant." Conservative substitution tables providing functionally similar amino acids are well known in the art. An example of a conservative substitution is the exchange of an amino acid in one of the following groups for another amino acid of the same group (U.S. Pat. No. 5,767,063 issued to Lee, et al.; *Kyte and Doolittle* (1982) *J. Mol. Biol.* 157: 105-132):

(1) Hydrophobic: Norleucine, Ile, Val, Leu, Phe, Cys, or Met;
(2) Neutral hydrophilic: Cys, Ser, Thr;
(3) Acidic: Asp, Glu;
(4) Basic: Asn, Gln, His, Lys, Arg;
(5) Residues that influence chain orientation: Gly, Pro;
(6) Aromatic: Trp, Tyr, Phe;
(7) Small amino acids: Gly, Ala, Ser.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health of the patient, the method route and dose of administration and the severity of side effects (see, e.g., U.S. Pat. No. 5,888,530 issued to Netti, et al.). An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject (see, e.g., Maynard, et al. (1996) *A Hand-* book of SOPs for Good Clinical Practice, Interpharm Press, Boca Raton, Fla.; Dent (2001) Good Laboratory and Good Clinical Practice, Urch Publ., London, UK). An effective amount of PEG-IL-10 would be an amount sufficient to reduce a tumor volume, inhibit tumor growth, prevent metastasis, or increase CD8+ T cell infiltration in to the tumor site.

"Exogenous" refers to substances that are produced outside an organism, cell, or human body, depending on the context. "Endogenous" refers to substances that are produced within a cell, organism, or human body, depending on the context.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist irradication by the immune system. "Cancerous condition" includes, e.g., cancer, cancer cells, tumors, angiogenesis, and precancerous conditions such as dysplasia.

"Inhibitors" and "antagonists" or "activators" and "agonists" refer to inhibitory or activating molecules, respectively, e.g., for the activation of, e.g., a ligand, receptor, cofactor, gene, cell, tissue, or organ. A modulator of, e.g., a gene, a receptor, a ligand, or a cell, is a molecule that alters an activity of the gene, receptor, ligand, or cell, where activity can be activated, inhibited, or altered in its regulatory properties. The modulator may act alone, or it may use a cofactor, e.g., a protein, metal ion, or small molecule Inhibitors are compounds that decrease, block, prevent, delay activation, inactivate, desensitize, or down regulate, e.g., a gene, protein, ligand, receptor, or cell. Activators are compounds that increase, activate, facilitate, enhance activation, sensitize, or up regulate, e.g., a gene, protein, ligand, receptor, or cell. An inhibitor may also be defined as a composition that reduces, blocks, or inactivates a constitutive activity. An "agonist" is a compound that interacts with a target to cause or promote an increase in the activation of the target. An "antagonist" is a compound that opposes the actions of an agonist. An antagonist prevents, reduces, inhibits, or neutralizes the activity of an agonist. An antagonist can also prevent, inhibit, or reduce constitutive activity of a target, e.g., a target receptor, even where there is no identified agonist.

To examine the extent of inhibition, for example, samples or assays comprising a given, e.g., protein, gene, cell, or organism, are treated with a potential activator or inhibitor and are compared to control samples without the inhibitor. Control samples, i.e., not treated with antagonist, are assigned a relative activity value of 100% Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., an indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) Ann. Clin. Lab. Sci. 30:145-158; Hood and Cheresh (2002) Nature Rev. Cancer 2:91-100; Timme, et al. (2003) Curr. Drug Targets 4:251-261; Robbins and Itzkowitz (2002) Med. Clin. North Am. 86:1467-1495; Grady and Markowitz (2002) Annu. Rev. Genomics Hum. Genet. 3:101-128; Bauer, et al. (2001) Glia 36:235-243; Stanimirovic and Satoh (2000) Brain Pathol. 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least 10 times the control.

A composition that is "labeled" is detectable, either directly or indirectly, by spectroscopic, photochemical, biochemical, immunochemical, isotopic, or chemical methods. For example, useful labels include $^{32}P$, $^{33}P$, $^{35}S$, $^{14}C$, $^{3}H$, $^{125}I$ stable isotopes, fluorescent dyes, electron-dense reagents, substrates, epitope tags, or enzymes, e.g., as used in enzyme-linked immunoassays, or fluorettes (see, e.g., Rozinov and Nolan (1998) Chem. Biol. 5:713-728).

"Ligand" refers, e.g., to a small molecule, peptide, polypeptide, and membrane associated or membrane-bound molecule, or complex thereof, that can act as an agonist or antagonist of a receptor. "Ligand" also encompasses an agent that is not an agonist or antagonist, but that can bind to the receptor without significantly influencing its biological properties, e.g., signaling or adhesion. Moreover, "ligand" includes a membrane-bound ligand that has been changed, e.g., by chemical or recombinant methods, to a soluble version of the membrane-bound ligand. By convention, where a ligand is membrane-bound on a first cell, the receptor usually occurs on a second cell. The second cell may have the same or a different identity as the first cell. A ligand or receptor may be entirely intracellular, that is, it may reside in the cytosol, nucleus, or some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway.

"Small molecules" are provided for the treatment of physiology and disorders of tumors and cancers. "Small molecule" is defined as a molecule with a molecular weight that is less than 10 kD, typically less than 2 kD, and preferably less than 1 kD. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins are described (see, e.g., Casset, et al. (2003) *Biochem. Biophys. Res. Commun.* 307:198-205; Muyldermans (2001) *J. Biotechnol.* 74:277-302; Li (2000) *Nat. Biotechnol.* 18:1251-1256; Apostolopoulos, et al. (2002) *Curr. Med. Chem.* 9:411-420; Monfardini et al. (2002) *Curr. Pharm. Des.* 8:2185-2199; Domingues, et al. (1999) *Nat. Struct. Biol.* 6:652-656; Sato and Sone (2003) *Biochem. J.* 371:603-608; U.S. Pat. No. 6,326,482 issued to Stewart, et al.).

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®.; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL® Bristol-Myers Squibb Oncology, Princeton, N.J.) and doxetaxel (Taxotere™, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and antiandrogens such as flutamide, nilutamide, bicalutamide, leuprolide, and goserelin; and pharmaceutically acceptable salts, acids or derivatives of any of the above "Specifically" or "selectively" binds, when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two fold greater, preferably at least ten times greater, more preferably at least 20-times greater, and most preferably at least 100-times greater than the affinity with any other antibody, or binding composition derived thereof. In a preferred embodiment the antibody will have an affinity that is greater than about $10^9$ liters/mol, as determined, e.g., by Scatchard analysis (Munsen, et al. (1980) *Analyt. Biochem.* 107:220-239).

"Interleukin-10" or "IL-10", as used herein, whether conjugated to a polyethylene glycol, or in a non-conjugated form, is a protein comprising two subunits nocovalently joined to form a homodimer. As used herein, unless otherwise indicated "interleukin-10" and "IL-10" can refer to human or mouse IL-10 (Genbank Accession Nos. NP 000563; M37897; or U.S. Pat. No. 6,217,857) which are also referred to as "hIL-10" or "mIL-10".

"Pegylated IL-10" or "PEG-IL-10" is an IL-10 molecule having one or more polyethylene glycol molecules covalently attached to one or more than one amino acid residue of the IL-10 protein via a linker, such that the attachment is stable. The terms "monopegylated IL-10" and "mono-PEG-IL-10", mean that one polyethylene glycol molecule is covalently attached to a single amino acid residue on one subunit of the IL-10 dimer via a linker. The average molecular weight of the PEG moiety is preferably between about 5,000 and about 50,000 daltons. The method or site of PEG attachment to IL-10 is not critical, but preferably the pegylation does not alter, or only minimally alters, the activity of the biologically active molecule. Preferably, the increase in half-life is greater than any decrease in biological activity. For PEG-IL-10, biological activity is typically measured by assessing the levels of inflammatory cytokines (e.g., TNFα, IFNγ) in the serum of subjects challenged with a bacterial antigen (lipopolysaccharide, LPS) and treated with PEG-IL-10, as described in U.S. Pat. No. 7,052,686.

As used herein, "serum half-life", abbreviated "$t_{1/2}$", means elimination half-life, i.e., the time at which the serum concentration of an agent has reached one-half its initial or maximum value. The term "increased serum half-life" used herein in reference to a synthetic agent means that the synthetic agent is cleared at a slower rate than either the non-synthetic, endogenous agent or the recombinantly produced version thereof.

II. General

The present invention provides methods of treating proliferative disorders, e.g., cancer, tumors, etc., with a pegylated-IL-10. IL-10 induces cytotoxic activity of CD8 T-cells, antibody production of B-cell and suppresses macrophage activity and tumor promoting inflammation (see, Chen and Zlotnik (1991) *J. Immunol.* 147:528-534; Groux, et al. (1999) *J. Immunol.* 162:1723-1729; and Bergman, et al. (1996) *J. Immunol.* 157:231-238). The regulation of CD8 cells is dose dependent, wherein higher doses induce stronger cytotoxic responses, however, the utility of recombinant hIL-10 is limited by its short half life. PEG-IL-10 showed an unexpected property of increasing the infiltration of CD8+ T cells to a tumor, as well as increasing the expression of inflammatory cytokines that play a role in tumor immunity. Treatment with PEG-IL-10 should therefore provide a significant improvement for tumor treatment.

III. Polyethylene Glycol ("PEG")

Polyethylene glycol ("PEG") is a chemical moiety which has been used in the preparation of therapeutic protein products. The verb "pegylate" means to attach at least one PEG molecule to another molecule, e.g. a therapeutic protein. For example Adagen, a pegylated formulation of adenosine deaminase, is approved for treating severe combined immunodeficiency disease; pegylated superoxide dismutase has been in clinical trials for treating head injury; pegylated alpha interferon has been tested in phase I clinical trials for treating hepatitis; pegylated glucocerebrosidase and pegylated hemoglobin are reported to have been in preclinical testing. The attachment of polyethylene glycol has been shown to protect against proteolysis (see, e.g., Sada, et al., (1991) *J. Fermentation Bioengineering* 71:137-139).

In its most common form, PEG is a linear or branched polyether terminated with hydroxyl groups and having the general structure:

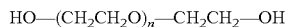

$$HO-(CH_2CH_2O)_n-CH_2CH_2-OH$$

To couple PEG to a molecule (polypeptides, polysaccharides, polynucleotides, and small organic molecules) it is necessary to activate the PEG by preparing a derivative of the PEG having a functional group at one or both termini. The most common route for PEG conjugation of proteins has been to activate the PEG with functional groups suitable for reaction with lysine and N-terminal amino acid groups. In particular, the most common reactive groups involved in coupling of PEG to polypeptides are the alpha or epsilon amino groups of lysine.

The reaction of a pegylation linker with a protein leads to the attachment of the PEG moiety predominantly at the following sites: the alpha amino group at the N-terminus of the protein, the epsilon amino group on the side chain of lysine residues, and the imidazole group on the side chain of histidine residues. Since most recombinant protein possess a single alpha and a number of epsilon amino and imidazole groups, numerous positional isomers can be generated depending on the linker chemistry.

Two widely used first generation activated monomethoxy PEGs (mPEGs) were succinimdyl carbonate PEG (SC-PEG; see, e.g., Zalipsky, et al. (1992) *Biotehnol. Appl. Biochem* 15:100-114; and Miron and Wilcheck (1993) *Bioconjug. Chem.* 4:568-569) and benzotriazole carbonate PEG (BTC-PEG; see, e.g., Dolence, et al. U.S. Pat. No. 5,650,234), which react preferentially with lysine residues to form a carbamate linkage, but are also known to react with histidine and tyrosine residues. The linkage to histidine residues on IFNα has been shown to be a hydrolytically unstable imidazolecarbamate linkage (see, e.g., Lee and McNemar, U.S. Pat. No. 5,985,263).

Second generation PEGylation technology has been designed to avoid these unstable linkages as well as the lack of selectivity in residue reactivity. Use of a PEG-aldehyde linker targets a single site on the N-terminus of a polypeptide through reductive amination. IL-10 may be pegylated using different types of linkers and pH to arrive at a various forms of a pegylated molecule (see, e.g., U.S. Pat. No. 5,252,714, U.S. Pat. No. 5,643,575, U.S. Pat. No. 5,919,455, U.S. Pat. No. 5,932,462, U.S. Pat. No. 5,985,263, U.S. Pat. No. 7,052,686).

IV. Biological Activity of PEG-IL-10

Human IL-10 induces rapid development of neutralizing antibodies when administered to immunocompetent mice. To avoid this type of neutralization, subcutaneous administration of PEG-hIL-10 was given to mice deficient in B-cells, i.e., mice unable to mount an antibody response. Well established syngeneic tumors in these immunodeficient mice were either significantly delayed in growth or rejected completely by PEG-hIL-10. The tumor growth restriction or inhibition was dependent on both CD4 and CD8 T-cells. Upon depletion of CD8 cells, the inhibitory effect of PEG-hIL-10 was completely abrogated. Thus, PEG-hIL-10 induces CD8 mediated cytotoxic responses.

Further analysis of tumor tissue showed that PEG-IL-10 increased the infiltration of CD8+ T cells into the tumor at a level greater than that of non-pegylated IL-10. The level of inflammatory cytokine expression by the infiltrating CD8 cells was also higher with PEG-IL-10 treatment as compared to non-pegylated IL-10 treatment. Treatment of tumor patients with PEG-IL-10 should induce a significant antitumor response and confer a significant therapeutic benefit.

An IL-10 protein used in the present invention contains an amino acid sequence that shares an observed homology of at least 75%, more preferably at least 85%, and most preferably at least 90% or more, e.g., at least 95%, with the sequence of a mature IL-10 protein, i.e., lacking any leader sequences. See, e.g., U.S. Pat. No. 6,217,857. Amino acid sequence homology, or sequence identity, is determined by optimizing residue matches and, if necessary, by introducing gaps as required. Homologous amino acid sequences are typically intended to include natural allelic, polymorphic and interspecies variations in each respective sequence. Typical homologous proteins or peptides will have from 25-100% homology (if gaps can be introduced) to 50-100% homology (if conservative substitutions are included) with the amino acid sequence of the IL-10 polypeptide. See Needleham et al., *J. Mol. Biol.* 48:443-453 (1970); Sankoff et al. in *Time Warps, String Edits, and Macromolecules: The Theory and Practice of Sequence Comparison*, 1983, Addison-Wesley, Reading, Mass.; and software packages from IntelliGenetics, Mountain View, Calif., and the University of Wisconsin Genetics Computer Group, Madison, Wis.

The IL-10 moiety in the PEG-IL-10 conjugates can be glycosylated or may be modified with unglycosylated muteins or other analogs, including the BCRF1 (Epstein Barr Virus viral IL-10) protein. Modifications of sequences encoding IL-10 can be made using a variety of techniques, e.g., site-directed mutagenesis [Gillman et al., *Gene* 8:81-97 (1979); Roberts et al., *Nature* 328:731-734 (1987)], and can be evaluated by routine screening in a suitable assay for IL-10 activity. Modified IL-10 proteins, e.g., variants, can vary from the naturally-occurring sequence at the-primary structure level. Such modifications can be made by amino acid insertions, substitutions, deletions and fusions. IL-10 variants can be prepared with various objectives in mind, including increasing serum half-life, reducing an immune response against the IL-10, facilitating purification or preparation, decreasing conversion of IL-10 into its monomeric subunits, improving therapeutic efficacy, and lessening the severity or occurrence of side effects during therapeutic use. The amino acid sequence variants are usually predetermined variants not found in nature, although others may be post-translational variants, e.g., glycosylated variants. Any variant of IL-10 can be used in this invention provided it retains a suitable level of IL-10 activity. In the tumor context, suitable IL-10 activity would be, e.g., CD8+ T cell infiltrate into tumor sites, expression of inflammatory cytokines such as IFNγ, IL-4, IL-6, IL-10, and RANK-L, from these infiltrating cells, increased levels of TNFα or IFNγ in biological samples, IL-10 used in this invention can be derived from a mammal, e.g. human or mouse. Human IL-10 (hIL-10) is preferred for treatment of humans in need of IL-10 treatment. IL-10 used in this invention is preferably a recombinant IL-10. Methods describing the preparation of human and mouse IL-10 can be found in U.S. Pat. No. 5,231,012. Also included are naturally occurring or conservatively substituted variants of human and mouse IL-10. In another embodiment of the present invention, IL-10 can be of viral origin. The cloning and expression of a viral IL-10 from Epstein Barr virus (BCRF1 protein) is disclosed in Moore et al., *Science* 248:1230 (1990).

IL-10 can be obtained in a number of ways using standard techniques known in the art, e.g., isolated and purified from culture media of activated cells capable of secreting the protein (e.g., T-cells), chemically synthesized, or recombinant techniques, (see, e.g., Merrifield, Science 233:341-47 (1986); Atherton et al., *Solid Phase Peptide Synthesis*, A Practical Approach, 1989, I.R.L. Press, Oxford; U.S. Pat. No. 5,231, 012 which teaches methods for the production of proteins having IL-10 activity, including recombinant and other synthetic techniques). Preferably, IL-10 protein is obtained from nucleic acids encoding the IL-10 polypeptide using recombinant techniques. Recombinant human IL-10 is also commercially available, e.g., from PeproTech, Inc., Rocky Hill, N.J.

PEG-IL-10 can be made using techniques well known in the art. Polyethylene glycol (PEG) can be synthesized as described, e.g., in Lundblad, R. L. et al. (1988) *Chemical Reagents for Protein Modification CRC Press, Inc., vol.* 1, pp. 105-125. PEG can be conjugated to IL-10 through use of a linker as described above. In certain embodiments, the PEG-IL-10 used in the invention is a mono-PEG-IL-10 in which one to nine PEG molecules are covalently attached via a linker to the alpha amino group of the amino acid residue at the N-terminus of one subunit of the IL-10 dimer.

IV. Therapeutic Compositions, Methods

PEG-IL-10 can be formulated in a pharmaceutical composition comprising a therapeutically effective amount of the IL-10 and a pharmaceutical carrier. A "therapeutically effective amount" is an amount sufficient to provide the desired therapeutic result. Preferably, such amount has minimal negative side effects. The amount of PEG-IL-10 administered to treat a condition treatable with IL-10 is based on IL-10 activity of the conjugated protein, which can be determined by IL-10 activity assays known in the art. The therapeutically effective amount for a particular patient in need of such treatment can be determined by considering various factors, such as the condition treated, the overall health of the patient, method of administration, the severity of side-effects, and the like. In the tumor context, suitable IL-10 activity would be, e.g., CD8 T cell infiltrate into tumor sites, expression of inflammatory cytokines such as IFNγ, IL-4, IL-6, IL-10, and RANK-L, from these infiltrating cells, increased levels of TNFα or IFNγ in biological samples.

The therapeutically effective amount of pegylated IL-10 can range from about 0.01 to about 100 μg protein per kg of body weight per day. Preferably, the amount of pegylated IL-10 ranges from about 0.1 to 20 μg protein per kg of body weight per day, more preferably from about 0.5 to 10 μg protein per kg of body weight per day, and most preferably from about 1 to 4 μg protein per kg of body weight per day. Less frequent administration schedules can be employed using the PEG-IL-10 of the invention since this conjugated form is longer acting than IL-10. The pegylated IL-10 is formulated in purified form and substantially free of aggregates and other proteins. Preferably, PEG-IL-10 is administered by continuous infusion so that an amount in the range of about 50 to 800 μg protein is delivered per day (i.e., about 1 to 16 μg protein per kg of body weight per day PEG-IL-10). The daily infusion rate may be varied based on monitoring of side effects and blood cell counts.

To prepare pharmaceutical compositions containing mono-PEG-IL-10, a therapeutically effective amount of PEG-IL-10 is admixed with a pharmaceutically acceptable carrier or excipient. Preferably the carrier or excipient is inert. A pharmaceutical carrier can be any compatible, non-toxic substance suitable for delivering the IL-10 compositions of the invention to a patient. Examples of suitable carriers include normal saline, Ringer's solution, dextrose solution, and Hank's solution. Non-aqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives, see, e.g., *Remington's Pharmaceutical Sciences* and *U.S. Pharmacopeia: National Formulary*, Mack Publishing Company, Easton, Pa. (1984). Formulations of therapeutic and diagnostic agents may be prepared by mixing with physiologically acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Compositions of the invention can be administered orally or injected into the body. Formulations for oral use can also include compounds to further protect the IL-10 from proteases in the gastrointestinal tract. Injections are usually intramuscular, subcutaneous, intradermal or intravenous. Alternatively, intra-articular injection or other routes could be used in appropriate circumstances.

When administered parenterally, pegylated IL-10 is preferably formulated in a unit dosage injectable form (solution, suspension, emulsion) in association with a pharmaceutical carrier. See, e.g., Avis et al., eds., *Pharmaceutical Dosage Forms: Parenteral Medications*, Dekker, N.Y. (1993); Lieberman et al., eds., *Pharmaceutical Dosage Forms: Tablets*, Dekker, N.Y. (1990); and Lieberman et al., eds., *Pharmaceutical Dosage Forms: Disperse Systems*, Dekker, N.Y. (1990). Alternatively, compositions of the invention may be introduced into a patient's body by implantable or injectable drug delivery system, e.g., Urquhart et al. *Ann. Rev. Pharmacol. Toxicol.* 24:199-236, (1984); Lewis, ed., *Controlled Release of Pesticides and Pharmaceuticals* Plenum Press, New York (1981); U.S. Pat. Nos. 3,773,919; 3,270,960; and the like. The pegylated IL-10 can be administered in aqueous vehicles such as water, saline or buffered vehicles with or without various additives and/or diluting agents.

An effective amount for a particular patient may vary depending on factors such as the condition being treated, the overall health of the patient, the method route and dose of administration and the severity of side affects (see, e.g., Maynard, et al. (1996) *A Handbook of SOPs for Good Clinical*

*Practice*, Interpharm Press, Boca Raton, Fla.; Dent (2001) *Good Laboratory and Good Clinical Practice*, Urch Publ., London, UK).

Typical veterinary, experimental, or research subjects include monkeys, dogs, cats, rats, mice, rabbits, guinea pigs, horses, and humans.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing a humoral response to the reagent.

Methods for co-administration or treatment with a second therapeutic agent, e.g., a cytokine, steroid, chemotherapeutic agent, antibiotic, or radiation, are well known in the art (see, e.g., Hardman, et al. (eds.) (2001) *Goodman and Gilman's The Pharmacological Basis of Therapeutics*, 10$^{th}$ ed., McGraw-Hill, New York, N.Y.; Poole and Peterson (eds.) (2001) *Pharmacotherapeutics for Advanced Practice: A Practical Approach*, Lippincott, Williams & Wilkins, Phila., Pa.; Chabner and Longo (eds.) (2001) *Cancer Chemotherapy and Biotherapy*, Lippincott, Williams & Wilkins, Phila., Pa.). An effective amount of therapeutic will decrease the symptoms, e.g., tumor size or inhibition of tumor growth, typically by at least 10%; usually by at least 20%; preferably at least about 30%; more preferably at least 40%, and most preferably by at least 50%.

VI. Uses

The present invention provides methods of treating a proliferative condition or disorder, e.g., cancer of the uterus, cervix, breast, prostate, testes, penis, gastrointestinal tract, e.g., esophagus, oropharynx, stomach, small or large intestines, colon, or rectum, kidney, renal cell, bladder, bone, bone marrow, skin, head or neck, skin, liver, gall bladder, heart, lung, pancreas, salivary gland, adrenal gland, thyroid, brain, e.g. gliomas, ganglia, central nervous system (CNS) and peripheral nervous system (PNS), and immune system, e.g., spleen or thymus. The present invention provides methods of treating, e.g., immunogenic tumors, non-immunogenic tumors, dormant tumors, virus-induced cancers, e.g., epithelial cell cancers, endothelial cell cancers, squamous cell carcinomas, papillomavirus, adenocarcinomas, lymphomas, carcinomas, melanomas, leukemias, myelomas, sarcomas, teratocarcinomas, chemically-induced cancers, metastasis, and angiogenesis. The invention also contemplates reducing tolerance to a tumor cell or cancer cell antigen, e.g., by modulating activity of a regulatory T cell (Treg) and or a CD8 T cell (see, e.g., Ramirez-Montagut, et al. (2003) *Oncogene* 22:3180-3187; Sawaya, et al. (2003) *New Engl. J. Med.* 349: 1501-1509; Farrar, et al. (1999) *J. Immunol.* 162:2842-2849; Le, et al. (2001) *J. Immunol.* 167:6765-6772; Cannistra and Niloff (1996) *New Engl. J. Med.* 334:1030-1038; Osborne (1998) *New Engl. J. Med.* 339:1609-1618; Lynch and Chapelle (2003) *New Engl. J. Med.* 348:919-932; Enzinger and Mayer (2003) *New Engl. J. Med.* 349:2241-2252; Forastiere, et al. (2001) *New Engl. J. Med.* 345:1890-1900; Izbicki, et al. (1997) *New Engl. J. Med.* 337:1188-1194; Holland, et al. (eds.) (1996) *Cancer Medicine Encyclopedia of Cancer*, 4$^{th}$ ed., Academic Press, San Diego, Calif.).

In some embodiments, the present invention provides methods for treating a proliferative condition, cancer, tumor, or precancerous condition such as a dysplasia, with PEG-IL-10 and at least one additional therapeutic or diagnostic agent. The additional therapeutic agent can be, e.g., a cytokine or cytokine antagonist, such as IL-12, interferon-alpha, or anti-epidermal growth factor receptor, doxorubicin, epirubicin, an anti-folate, e.g., methotrexate or fluoruracil, irinotecan, cyclophosphamide, radiotherapy, hormone or anti-hormone therapy, e.g., androgen, estrogen, anti-estrogen, flutamide, or diethylstilbestrol, surgery, tamoxifen, ifosfamide, mitolactol, an alkylating agent, e.g., melphalan or cis-platin, etoposide, vinorelbine, vinblastine, vindesine, a glucocorticoid, a histamine receptor antagonist, an angiogenesis inhibitor, radiation, a radiation sensitizer, anthracycline, vinca alkaloid, taxane, e.g., paclitaxel and docetaxel, a cell cycle inhibitor, e.g., a cyclin-dependent kinase inhibitor, a monoclonal antibody against another tumor antigen, a complex of monoclonal antibody and toxin, a T cell adjuvant, bone marrow transplant, or antigen presenting cells, e.g., dendritic cell therapy. Vaccines can be provided, e.g., as a soluble protein or as a nucleic acid encoding the protein (see, e.g., Le, et al., supra; Greco and Zellefsky (eds.) (2000) *Radiotherapy of Prostate Cancer*, Harwood Academic, Amsterdam; Shapiro and Recht (2001) *New Engl. J. Med.* 344:1997-2008; Hortobagyi (1998) *New Engl. J. Med.* 339:974-984; Catalona (1994) *New Engl. J. Med.* 331:996-1004; Naylor and Hadden (2003) *Int. Immunopharmacol.* 3:1205-1215; The Int. Adjuvant Lung Cancer Trial Collaborative Group (2004) *New Engl. J. Med.* 350:351-360; Slamon, et al. (2001) *New Engl. J. Med.* 344:783-792; Kudelka, et al. (1998) *New Engl. J. Med.* 338:991-992; van Netten, et al. (1996) *New Engl. J. Med.* 334:920-921).

Also provided are methods of treating extramedullary hematopoiesis (EMH) of cancer. EMH is described (see, e.g., Rao, et al. (2003) *Leuk. Lymphoma* 44:715-718; Lane, et al. (2002) *J. Cutan. Pathol.* 29:608-612).

The broad scope of this invention is best understood with reference to the following examples, which are not intended to limit the inventions to the specific embodiments.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

Examples

I. General Methods

Standard methods in molecular biology are described (Maniatis, et al. (1982) *Molecular Cloning, A Laboratory Manual*, Cold Spring Harbor Laboratory Press, Cold Spring Harbor, N.Y.; Sambrook and Russell (2001) *Molecular Cloning*, 3$^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausubel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies is described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol. 4*, John Wiley, Inc., New York). Methods for making PEG-IL-10 are described, e.g., in U.S. Pat. No. 7,052,686.

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry, $2^{nd}$ ed.*; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila. Pa.; Louis, et al. (2002) *Basic Histology: Text and Atlas*, McGraw-Hill, New York, N.Y.).

Methods for the treatment and diagnosis of cancer are described (see, e.g., Alison (ed.) (2001) *The Cancer Handbook*, Grove's Dictionaries, Inc., St. Louis, Mo.; Oldham (ed.) (1998) *Principles of Cancer Biotherapy, $3^{rd}$. ed.*, Kluwer Academic Publ., Hingham, Mass.; Thompson, et al. (eds.) (2001) *Textbook of Melanoma*, Martin Dunitz, Ltd., London, UK; Devita, et al. (eds.) (2001) *Cancer: Principles and Practice of Oncology, $6^{th}$ ed.*, Lippincott, Phila. Pa.; Holland, et al. (eds.) (2000) *Holland-Frei Cancer Medicine*, BC Decker, Phila., Pa.; Garrett and Sell (eds.) (1995) *Cellular Cancer Markers*, Humana Press, Totowa, N.J.; MacKie (1996) *Skin Cancer, $2^{nd}$ ed.*, Mosby, St. Louis; Moertel (1994) *New Engl. J. Med.* 330:1136-1142; Engleman (2003) *Semin. Oncol.* 30(3 Suppl. 8):23-29; Mohr, et al. (2003) *Onkologie* 26:227-233).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

II. Pegylated IL-10

IL-10 was dialiyzed against 10 mM sodium phosphate pH 7.0, 100 mM NaCl. The dialyzed IL-10 was diluted 3.2 times to a concentration of 4 mg/mL using the dialysis buffer. Prior to the addition of the linker, SC-PEG-12K (Delmar Scientific Laboratories, Maywood, Ill.), 1 volume of 100 mM Na-tetraborate at pH 9.1 was added into 9 volumes of the diluted IL-10 to raise the pH of the IL-10 solution to 8.6. The SC-PEG-12K linker was dissolved in the dialysis buffer and the appropriate volume of the linker solution (1.8 to 3.6 mole linker per mole of IL-10) was added inot the diluted IL-10 solution to start the pegylation reaction. The reaction was carried out at 5° C. in order to control the reate of the reaction. The reaction solution was mildly agitated during the pegylation reaction. When the mono-PEG-IL-10 yield as determined by size exclusion HPLC (SE-HPLC), was close to 40%, the reaction was stopped by adding 1M glycine solution to a final concentration of 30 mM. The pH of the reaction solution was slowly adjusted to 7.0 using an HCl solution and the reaction was 0.2 micron filtered and stored at −80° C.

Alternatively, mono-PEG-IL-10 is prepared using methoxy-PEG-aldehyde (PALD-PEG) as a linker (Inhale Therapeutic Systems Inc., Huntsville, Ala.). PALD-PEG can have molecular weights of 5 KDa, 12 KDa, or 20 KDa. IL-10 is dialyzed and diluted as described above, except the pH of the reaction buffer is between 6.3 and 7.5. Activated PALD-PEG linker is added to reaction buffer at a 1:1 molar ratio. Aqueous cyanoborohydride is added to the reaction mixture to a final concentration of 0.5 to 0.75 mM. The reaction is carried out at room temperature (18-25° C.) for 15-20 hours with mild agitation. The reaction is quenched with 1M glycine. Yields are analyzed by SE-HPLC. Mono-PEG-IL-10 is separated from unreacted IL-10, PEG linker, and di-PEG-IL-10 by gel filtration chromatography and characterized by rp-HPLC and bioassay (e.g., stimulation of IL-10 responsive cells or cell lines).

III. Tumor Models

Syngeneic mouse tumor cells were injected subcutaneously or intradermally at $10^4$, $10^5$ or $10^6$ cells per tumor inoculation. Ep2 mammary carcinoma, CT26 colon carcinoma, PDV6 squamous carcinoma of the skin and 4T1 breast carcinoma models were used (see, e.g., Langowski et al. (2006) *Nature* 442:461-465). Immunocompetent Balb/C or B cell deficient Balb/C mice were used. PEG-mIL-10 was administered to the immunocompetent mice, while PEG-hIL-10 treatment was used in the B-cell deficient mice. Tumors were allowed to reach a size of 100-250 mm³ before treatment was started. IL-10, PEG-mIL-10, PEG-hIL-10, or buffer control was administered subcutaneously at a site distant from the tumor implantation. Tumor growth was typically monitored twice weekly using electronic calipers.

IV. Tumor Analysis

Tumor tissues and lymphatic organs were harvested at various endpoints to measure mRNA expression for a number of inflammatory markers and to perform immunohistochemistry for several inflammatory cell marker. The tissues were snap frozen in liquid nitrogen and stored at −80° C. Primary tumor growth was typically monitored twice weekly using electronic calipers. Tumor volume was calculated using the formula (width×length/2) where length is the longer dimension. Tumors were allowed to reach a size of 90-250 mm³ before treatment was started.

V. Administration of IL-10 and/or PEG-IL-10 mIL-10 or PEG-mIL-10 was administered to the immunocompetent mice, while PEG-hIL-10 treatment was used in the B-cell deficient mice. mIL-10, PEG-mIL-10, PEG-hIL-10, or vehicle control was administered subcutaneously at a site distant from the tumor implant. PEG-mIL-10 used in these studies was prepared with the SC-PEG-12K linker. The biological activities of mIL-10 and PEG-m IL-10 were assessed by the application of a short-term proliferation bioassay that utilized MC/9, a mouse mast cell line, which expresses endogenous mIL-10 receptors (R1 and R2). The MC/9 cells proliferate in response to co-stimulation with mIL-4 and mIL-10 (MC/9's do not proliferate with only mIL-4 or mIL-10). Proliferation was measured by colorimetric means using Alamar Blue, a growth indicator dye based on detection of metabolic activity. The biological activity of recombinant or pegylated mIL-10 was assessed by the EC50 value, or the concentration of protein at which half-maximal stimulation is observed in a dose-response curve (Table 1).

TABLE 1

MC/9 Proliferation bioassay for the assessment of bioactivity of mIL-10 and PEG-mIL10 reagents used in these studies

| Protein | EC50 (ng/mL) in MC/9 Assay |
| --- | --- |
| mIL-10 | 0.5711 |
| PEG-mIL-10 | 4.039 |

Based on the MC/9 bioassay, the specific activity of the pegylated mIL-10 used in the experiments is approximately 7 fold lower than the activity of the mIL-10 used (Table 1).

PEG-mIL-10 was administered every second day to mice harboring Ep2 breast cancer tumors. Treatment was effective in reducing tumor size and induce tumor rejections.

TABLE 2

PEG mIL-10 reduces tumor size ($mm^3$) in Ep2 breast cancer model in Balb/C mice.

| Days after Inoculation | 11 | 15 | 18 | 21 | 25 | 27 | 33 |
| --- | --- | --- | --- | --- | --- | --- | --- |
| Control | 300 | 450 | 500 | 750 | 1300 | 1500 | 2700 |
| PEG-IL-10 | 300 | 400 | 310 | 280 | 250 | 50 | 0 |

Treatment with PEG-mIL-10 was also effective in reducing tumor size in PDV6, CT-26, and 4T1 syngeneic immune competent mouse tumor models (see Tables 3, 4, and 5.

TABLE 3

Study 04-M52 338: PEG mIL-10 beginning day 36 after implant reduces PDV6 tumor size ($mm^3$) in C57B/6 mice..

| Days after Inoculation | 36 | 38 | 42 | 44 | 46 | 48 | 52 |
| --- | --- | --- | --- | --- | --- | --- | --- |
| Control | 200 | 255 | 290 | 380 | 395 | 420 | 485 |
| PEG-mIL-10 | 210 | 265 | 200 | 190 | 155 | 110 | 55 |

TABLE 4

PEG mIL-10 beginning day 7 after implant reduces tumor size relative to vehicle control of CT26 tumors ($mm^3$) in BALB/c mice.

| Days after Inoculation | 10 | 15 | 17 | 20 | 22 | 24 |
| --- | --- | --- | --- | --- | --- | --- |
| Vehicle Control | 155 | 424 | 791 | 1274 | 1737 | 2170 |
| PEG-mIL-10 | 136 | 212 | 291 | 336 | 450 | 455 |

TABLE 5

IL-10 and PEG mIL-10 reduces tumor size ($mm^3$) of 4T1 breast carcinoma

| | Days of Treatment | | | |
| --- | --- | --- | --- | --- |
| | 20 | 24 | 29 | 33 |
| Control | 200 | 410 | 584 | 1000 |
| PEG-mIL-10 | 200 | 320 | 560 | 350 |
| IL-10 | 200 | 290 | 575 | 400 |

TABLE 6

Study 05-M52-496. 2 week treatment with mIL-10 and mPEG IL-10 beginning 19 days after implant reduces tumor size ($mm^3$) of 4T1 breast carcinoma.

| | Days after implant | | | |
| --- | --- | --- | --- | --- |
| | 20 | 24 | 29 | 33 |
| PBS | 200 | 410 | 584 | 1000 |
| PEG-mIL-10 | 200 | 320 | 560 | 350 |
| mIL-10 | 200 | 290 | 575 | 400 |

VI. Dose Titration Studies

In dose titration, studies tail vein bleeds were collected from representative mice of each group at times corresponding to the expected peak and trough dose levels. Serum harvested was assayed for mIL-10 concentrations using the Meso Scale Discovery platform which is based on multi-array technology; a combination of electrochemiluminescence detection and patterned arrays. A two-tailed unpaired student t-test was used to compare the mean tumor volume of mIL-10 or PEG-mIL-10 treated mice grouped by serum mIL-10 concentration with the mean tumor volume of their corresponding vehicle control group. A Welch's correction was used when two groups had unequal variance ($p<0.05$ from F-test).

Dose titrations of PEG-mIL-10 and mIL-10 in 4T1 breast carcinoma bearing mice show that control of primary tumor and lung metastases are dose titratable with both mIL-10 and with PEG-mIL-10. At any given dose PEG-mIL-10 is more effective than mIL-10 (Table 7). Twice daily treatment was started on Day 17 after implant, when the mean tumor volumes were 84-90 $mm^3$. Treatment groups consisted of 14 mice per group while the control groups had 8 mice in each group. Tris and Hepes buffers were the controls for mIL-10 and PEG mIL-10 respectively.

TABLE 7

Study 06-M175-1103. mIL-10 and PEG-mIL-10 reduce primary tumor size ($mm^3$) of 4T1 breast carcinoma in BALB/c mice in a dose-dependent manner.

| Days after Implant | 17 | 21 | 24 | 27 | 30 | 34 | 38 | 42 |
|---|---|---|---|---|---|---|---|---|
| Tris Vehicle control | 90 | 184 | 288 | 448 | 560 | 861 | 1126 | 1248 |
| Hepes Vehicle control | 90 | 215 | 344 | 476 | 658 | 940 | 1261 | 1520 |
| PEG-mIL-10 (0.5 mg/kg) | 86 | 107 | 117 | 129 | 150 | 165 | 204 | 195 |
| PEG-mIL-10 (0.1 mg/kg) | 84 | 112 | 142 | 152 | 224 | 256 | 286 | 356 |
| PEG-mIL-10 (0.01 mg/kg) | 85 | 140 | 200 | 240 | 288 | 462 | 627 | 773 |
| PEG-mIL-10 (0.001 mg/kg) | 88 | 168 | 239 | 262 | 373 | 532 | 729 | 942 |
| mIL-10 (1.0 mg/kg) | 85 | 117 | 168 | 207 | 256 | 350 | 446 | 497 |
| mIL-10 (0.1 mg/kg) | 84 | 136 | 180 | 251 | 337 | 424 | 641 | 704 |
| mIL-10 (0.01 mg/kg) | 86 | 121 | 165 | 231 | 331 | 436 | 631 | 809 |

Dose titrations of PEG-mIL-10 and mIL-10 in PDV6 squamous cell carcinoma bearing mice show that control of primary tumor is dose titratable with both mIL-10 and with PEG-mIL-10, though at any given dose PEG-mIL-10 is more effective than mIL-10 (Table 8). The high dose PEG-mIL-10 treatment resulted in a near 100% tumor regression and subsequent resistance to re-challenge. (Table 9). Twice daily treatment was started on Day 23 after implant, when the mean tumor volumes were 107-109 $mm^3$ and continued through day 55 for all mIL10. treated groups and 0.01 mg/kg PEG mIL-10 treated group. 0.1 mg/kg PEG-mIL-10 treatment was stopped on day 48 when 100% tumor regression was seen while the remaining groups were treated until day 51. Treatment groups consisted of 10 mice per group while each vehicle control contained 6 mice. Tris buffer and Hepes buffer were the vehicle control for mIL-10 and PEG mIL-10 respectively. Re-implant was done 85 days after the primary implant and 4 weeks after last PEG-mIL10 treatment. There were 10 mice per group.

VII. Lung Metastasis Studies

Lung metastases in the 4T1 breast carcinoma model, were either quantified macroscopically after lung resection (Table 10) or by counting the lung metastatic colonies after culture (Table 11) as described in Current Protocols in Immunology (Section 20.2.4) John Wiley and Sons, Inc., New York; Harlow and Lane (1999). Briefly, lungs harvested from a 4T1 tumor-bearing mouse were minced and digested with a collagenase/elastase cocktail followed by culture in a limiting dilution assay, in medium containing 6-thioguanine Only 4T1 cells are 6-thioguanine resistant and can be quantified by counting the number of colonies after 10-14 days of culture. Twice daily treatment was started on Day 17 after implant, when the mean tumor volumes were 84-90 $mm^3$. Tris and Hepes buffers were the controls for mIL-10 and PEG mIL-10 respectively. Lung metastases measured as number of metastatic colonies cultured per lung.

TABLE 8

Study 06-M52-1106. mIL-10 and PEG-mIL-10 reduce tumor size ($mm^3$) of PDV6 squamous cell carcinoma in C57Bl6/J mice in a dose dependent manner.

| Days after Implant | 23 | 27 | 30 | 33 | 36 | 40 | 43 | 47 | 51 | 55 |
|---|---|---|---|---|---|---|---|---|---|---|
| Tris Vehicle control | 111 | 179 | 232 | 318 | 412 | 493 | 635 | 848 | 958 | |
| Hepes Vehicle control | 107 | 210 | 293 | 433 | 541 | 653 | 712 | 761 | 986 | |
| PEG-mIL-10 (0.1 mg/kg) | 108 | 99 | 55 | 31 | 17 | 11 | 3 | 1 | 1 | 1 |
| PEG-mIL-10 (0.01 mg/kg) | 107 | 131 | 92 | 97 | 95 | 114 | 119 | 123 | 183 | 228 |
| PEG-mIL-10 (0.001 mg/kg) | 109 | 191 | 191 | 241 | 327 | 455 | 535 | | | |
| mIL-10 (1.0 mg/kg) | 107 | 129 | 144 | 143 | 124 | 87 | 51 | 36 | 52 | 75 |
| mIL-10 (0.1 mg/kg) | 107 | 85 | 85 | 88 | 117 | 121 | 130 | 143 | 182 | 217 |
| mIL-10 (0.01 mg/kg) | 107 | 120 | 150 | 146 | 196 | 244 | 262 | 263 | 249 | 250 |

TABLE 9

Study 06-M52-1106. C57Bl/6J mice that have cleared PDV6 squamous cell carcinoma tumors after 3 weeks of PEG-mIL-10 treatment are resistant to re-implant in the absence of additional treatment..

| Days after Implant | 0 | 16 | 21 | 28 | 36 | 49 | % mice that are tumor positive |
|---|---|---|---|---|---|---|---|
| Vehicle Control | 0 | 113 | 145 | 188 | 418 | 761 | 100 |
| PEG-mIL-10 (0.1 mg/kg) | 0 | 0.3 | 0 | 7 | 16 | 47 | 10 |

TABLE 10

Study 05-M52-496. 2 week treatment with mIL-10 and PEG-mIL-10 beginning 19 days after implant reduces metastasis of 4T1 breast carcinoma (measured as number of lung metastases per mouse)

| Lung Metastasis 33 days after Inoculation | Vehicle Control | mIL-10 | PEG-mIL-10 |
|---|---|---|---|
| Mouse #1 | 7 | 0 | 0 |
| Mouse #2 | 7 | 0 | 0 |
| Mouse #3 | 7 | 0 | 0 |
| Mouse #4 | 8 | 0 | 0 |
| Mouse #5 | 20 | 4 | 0 |

TABLE 11

Study 06-M175-1103. mIL-10 and PEG-mIL-10 reduce lung metastases of 4T1 breast carcinoma in BALB/c mice in a dose-dependent manner.

Lung Metastases 42-45 days after Implant
Colonies per lung (×10³)

| Mouse | Tris buffer vehicle control | Hepes buffer vehicle control | mIL-10 1.0 mg/kg | mIL-10 0.1 mg/kg | mIL-10 0.01 mg/kg | PEG-mIL-10 0.5 mg/kg | PEG-mIL-10 0.1 mg/kg | PEG-mIL-10 0.01 mg/kg | PEG-mIL-10 0.001 mg/kg |
|---|---|---|---|---|---|---|---|---|---|
| 1 | 362 | 481 | 76 | 116 | 1064 | 7.1 | 89 | 0.43 | 366 |
| 2 | 2.12 | 533 | 20 | 5.6 | 150 | 1.0 | 0.7 | 234 | 212 |
| 3 | 152 | 264 | 28.1 | 8.1 | 67.4 | 0.4 | 0.01 | 377 | 0.6 |
| 4 | 0.4 | 218 | 1.2 | 137 | 18 | 1.5 | 223 | 315 | 586 |
| 5 | 1000 | 517 | 45.7 | 257 | 77 | 0.3 | 0.07 | 0.54 | 486 |
| 6 | 474 | 93 | 21.7 | 2.72 | 1.2 | 0.02 | 10.1 | 1.67 | 844 |
| 7 | 524 | 1000 | 4.4 | 364 | 285 | 0 | 7.6 | 68 | 6.5 |
| 8 | 1000 | 1026 | 128.6 | 772 | 9.7 | 0.002 | 1.85 | 27 | 265 |
| 9 | | | 13.3 | 348 | 878 | 0.3 | 0.01 | 139 | 338 |
| 10 | | | 51.2 | 204 | 45 | 0.03 | 0.01 | 177 | 824 |
| 11 | | | 9.4 | 49 | 56 | 0.01 | 2.68 | 597 | 263 |
| 12 | | | 0.1 | 635 | 17.1 | 240 | 0.01 | 7.4 | |
| 13 | | | 5.1 | 19.7 | 1014 | 0.02 | 2.94 | 0.01 | |
| 14 | | | 0.02 | 750 | 72.2 | 0.01 | 0.01 | 0.01 | |
| Median | 418.0 | 499.0 | 16.7 | 170.5 | 69.8 | 0.17 | 1.28 | 47.5 | 338.0 |
| Mean | 502.0 | 579.0 | 28.9 | 262.0 | 268.2 | 17.9 | 24.1 | 138.9 | 381.0 |
| S.D. | 519.0 | 467.0 | 36.5 | 276.9 | 397.1 | 64.0 | 61.8 | 183.7 | 284.0 |

Administering PEG-mIL-10 or IL-10 to 4T1 breast carcinoma bearing mice reduces the rate of metastasis and increases CD8 T-cell infiltration and expression of immune stimulatory cytokines, as measured by quantitative RT-PCR. (Tables 12 and 13). The number of infiltrating CD8+ T-cells was counted from representative sections of several tumors stained by immunohistochemistry for the CD8 surface marker and verified by staining with anti-CD3 and anti-TCRαβ antibodies.

TABLE 12

IL-10 and PEG mIL-10 induce CD8+ T-cell infiltration in 4T1 carcinoma

| | control | IL-10 | PEG-IL-10 |
|---|---|---|---|
| Average Number of CD8+ Cells/Field | 6.4 | 25.8 | 39.2 |

PEG-mIL-10 is more effective than IL-10 in the induction of inflammatory cytokines Total RNA from homogenized tumor samples was extracted and reverse transcribed as previously described (see, e.g., Homey, et al. (2000) *J. Immunol.* 164:3465-3470). Complementary DNA was quantitatively analyzed for expression of cytokines by the fluorgenic 5'-nuclease PCR assay (see, e.g., Holland, et al. (1991) *Proc. Natl. Acad. Sci.* 88:7276-7280). Specific PCR products were continuously measured by means of an ABI PRISM 7700 Sequence Detection System (Applied Biosystems) during 40 cycles. Values were normalized to ubiquitin. Log-transformed data was subjected to Kruskal-Wallis statistical analysis (median method). The expression level (log transformed) corresponds to the amount of inflammatory cytokine expressed in the tumor sample, such that the higher the expression level (log transformed), the greater the amount of inflammatory cytokine expressed in the tumor sample.

TABLE 13

Administered PEG-mIL-10 induces sustained levels of inflammatory cytokines in 4T1 carcinoma 24 h after dose administration.

| Cytokine | control | IL-10 | PEG-mIL-10 |
|---|---|---|---|
| IFNγ | 36.04 | 68.51 | 98.96 |
| IL-4 | 7.77 | 13.13 | 40.32 |
| IL-6 | 43.64 | 50.59 | 111.98 |
| IL-10 | 9.94 | 41.62 | 106.16 |
| RANK-Ligand | 19.14 | 36.13 | 46.08 |

V. Depletion of Immune Cells

CD4+ and CD8+ T-cells were depleted by antibody mediated elimination. 250 ug of CD4 or CD8 specific antibodies were injected weekly for this purpose. Cell depletions were verified using FACS and IHC analysis.

Depletion of CD4+ T cells in B cell deficient BALB/c mice (C.129-Igh-6$^{tm1Cgn}$) with CD4 antibodies inhibits PEG-hIL-10 function on tumors (Table 14).

TABLE 14

PEG-hIL-10 treatment beginning 8 days after tumor implant fails to reduce tumor size (mm³) of CT-26 colon carcinoma after CD4 depletion in B cell deficient BALB/c mice (C.129-Igh-6$^{tm1Cgn}$).

| | Days after Implant | | | | |
|---|---|---|---|---|---|
| | 8 | 10 | 13 | 19 | 27 |
| PBS | 173 | 322 | 391 | 841 | 1979 |
| PEG-hIL-10 | 184 | 276 | 251 | 602 | 1332 |

Depletion of CD8 T-cells completely inhibits the effect of PEG mIL-10 on syngeneic tumor (Table 15).

TABLE 15

PEG-hIL-10 treatment beginning 8 days after tumor implant fails to reduce tumor size (mm$^3$) of CT-26 colon carcinoma after CD8 depletion in B cell deficient BALB/c mice.

| | Days after Implant | | | | |
|---|---|---|---|---|---|
| | 8 | 10 | 13 | 19 | 27 |
| PBS | 151 | 335 | 584 | 1434 | 2746 |
| PEG-hIL-10 | 226 | 575 | 1047 | 2449 | 4799 |

VI. Combination Therapies

PEG-IL-10 is administered in combination with known chemotherapeutic agents. The chemotherapeutic can be administered prior to, concurrently with, or subsequent to administration of PEG-IL-10. Examples of chemotherapeutics and dosage ranges are provided in Table 16.

TABLE 16

Chemotherapeutic dosage ranges

| Chemotherapeutic Agent | Dosage Range |
|---|---|
| Temozolomide | 5 mgs-250 mgs |
| Gemcitabine | 200 mgs-1 gm |
| Doxorubicin | 1 mg/m$^2$-50 mg/m$^2$ |
| Interferon-alpha | 1 µg/kg-300 µg/kg |

Co-administration of PEG-IL-10 may permit use of lower, less toxic dosages of the chemotherapeutics, thus avoiding known side effects.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A method of inhibiting or reducing growth of a tumor or cancer in a subject in need thereof, the method comprising:
    administering to the subject an effective amount of a pegylated interleukin-10 (PEG-IL-10), wherein the cancer or tumor is lymphoma.

2. The method of claim 1, wherein the subject is human.

3. The method of claim 2, wherein the PEG-IL-10 is human PEG-IL-10 (PEG-hIL-10).

4. The method of claim 1, wherein the PEG-IL-10 comprises a methoxy-PEG-aldehyde (PALD-PEG) linker.

5. The method of claim 2, wherein the PEG-IL-10 comprises a methoxy-PEG-aldehyde (PALD-PEG) linker.

6. The method of claim 3, wherein the PEG-IL-10 comprises a methoxy-PEG-aldehyde (PALD-PEG) linker.

7. The method of claim 1, wherein the PEG-IL-10 is co-administered with at least one chemotherapeutic agent.

8. The method of claim 7, wherein the chemotherapeutic agent is at least one of cyclophosphamide, doxorubicin, vincristine, fludarabine, carboplatin, etoposide, mitoxantrone, ifosfamide, cytarabine, cisplatin, and bleomycin.

9. A method of treating a subject suffering from lymphoma, the method comprising:
    administering to the subject an effective amount of a pegylated interleukin-10 (PEG-IL-10).

10. The method of claim 9, wherein the subject is human.

11. The method of claim 10, wherein the PEG-IL-10 is human PEG-IL-10 (PEG-hIL-10).

12. The method of claim 9, wherein the PEG-IL-10 comprises a methoxy-PEG-aldehyde (PALD-PEG) linker.

13. The method of claim 10, wherein the PEG-IL-10 comprises a methoxy-PEG-aldehyde (PALD-PEG) linker.

14. The method of claims 11, wherein the PEG-IL-10 comprises a methoxy-PEG-aldehyde (PALD-PEG) linker.

15. The method of claim 9, wherein the PEG-IL-10 is co-administered with at least one chemotherapeutic agent.

16. The method of claim 15, wherein the chemotherapeutic agent is at least one of cyclophosphamide, doxorubicin, vincristine, fludarabine, carboplatin, etoposide, mitoxantrone, ifosfamide, cytarabine, cisplatin, and bleomycin.

* * * * *